(12) United States Patent
Choi et al.

(10) Patent No.: US 11,459,311 B2
(45) Date of Patent: Oct. 4, 2022

(54) PHARMACEUTICAL COMPOSITION CONTAINING INDIRUBIN DERIVATIVE AS ACTIVE INGREDIENT

(71) Applicant: CK Regeon Inc., Seoul (KR)

(72) Inventors: Kang-Yell Choi, Seoul (KR); Gyoonhee Han, Seoul (KR); Jeong-Ha Hwang, Seoul (KR); Sehee Choi, Seoul (KR); Changmok Oh, Seoul (KR)

(73) Assignee: CK REGEON INC., Seoul (KR)

( * ) Notice: Subject to any disclaimer, the term of this patent is extended or adjusted under 35 U.S.C. 154(b) by 0 days.

(21) Appl. No.: 16/606,089

(22) PCT Filed: Apr. 10, 2018

(86) PCT No.: PCT/KR2018/004201
§ 371 (c)(1),
(2) Date: Oct. 17, 2019

(87) PCT Pub. No.: WO2018/194309
PCT Pub. Date: Oct. 25, 2018

(65) Prior Publication Data
US 2020/0223824 A1 Jul. 16, 2020

(30) Foreign Application Priority Data

Apr. 18, 2017 (KR) .......................... 10-2017-0049658

(51) Int. Cl.
*C07D 403/04* (2006.01)
*A61P 19/00* (2006.01)
*A61P 19/10* (2006.01)

(52) U.S. Cl.
CPC ............ *C07D 403/04* (2013.01); *A61P 19/10* (2018.01)

(58) Field of Classification Search
None
See application file for complete search history.

(56) References Cited

U.S. PATENT DOCUMENTS

| 7,572,923 | B2 | 8/2009 | Kim et al. |
| 8,859,783 | B2 | 10/2014 | Kim et al. |
| 10,149,833 | B2 | 12/2018 | Choi et al. |
| 2010/0247494 | A1 | 9/2010 | Gregory |
| 2015/0259288 | A1 | 9/2015 | Nam |
| 2016/0243077 | A1* | 8/2016 | Brown ................ C07K 16/40 |
| 2020/0016087 | A1* | 1/2020 | Wu .................... A61K 9/5153 |

FOREIGN PATENT DOCUMENTS

| EP | 2518139 | 10/2012 |
| KR | 20050077173 | 8/2005 |
| KR | 20100040488 | 4/2010 |
| KR | 20110091074 | 8/2011 |
| KR | 101493324 | 2/2015 |
| KR | 20160131199 | 11/2016 |
| WO | 2011096676 | 8/2011 |
| WO | 2015005603 | 1/2015 |

OTHER PUBLICATIONS

Chemical Abstract Registry No. 2169268-54-4, indexed in the Registry File on STN CAS Online Jan. 3, 2018.*
Saito et al., Synthesis of methoxy- and bromo-substituted indirubins and their activities on apoptosis induction in human neuroblastoma cells. Bioorganic & Medicinal Chemistry Letters, 2011, 21, 5370-5373.*
Zahoor et al., Indirubin-3'-Oxime Reverses Bone Loss in Ovariectomized and Hindlimb-Unloaded Mice Via Activation of the Wnt/β-Catenin Signaling. Journal of Bone and Mineral Research, 2014, 29, 1196-1205.*
Polychronopoulos et al., Structural Basis for the Synthesis of Indirubins as Potent and Selective Inhibitors of Glycogen Synthase Kinase-3 and Cyclin-Dependent Kinases. Journal of Medicinal Chemistry, 2004, 47, 935-946.*
Gillespie et al., GSK-3 Function in Bone Regulates Skeletal Development, Whole-Body Metabolism, and Male Life Span. Endocrinology, 2013, 154, 1-27.*
Zahoor Muhammad et al: "Indirubin-3'-oxime, an activator of Wnt/[beta]-catenin signaling, enhances osteogenic commitment of ST2 cells and restores bone loss in high-fat diet-induced obese m", Bone, Pergamon Press., Oxford, GB, May 9, 2014, 9 pages.
U. Krause et al: "Pharmaceutical modulation of canonical Wnt signaling in multipotent stromal cells for improved osteoinductive therapy", Proceedings of the National Academy of Sciences, Feb. 11, 2010.
Extended European Search Report for European Patent Application No. 18787683.4, dated Dec. 9, 2020, 10 pages.
Beauchard A et al: "Synthesis and kinase inhibitory activity of novel substituted indigoids" Bioorganic & Medicinal Chemistry, Elsevier, NL, Sep. 1, 2009.

(Continued)

*Primary Examiner* — Po-Chih Chen
(74) *Attorney, Agent, or Firm* — NSIP Law (57) ABSTRACT

A composition for promoting longitudinal bone growth, according to the present invention, promotes the proliferation of the chondrocytes and the differentiation of the osteoblasts and has effects of simultaneously increasing longitudinal bone length and thickness (bone density), and thus has an advantage of being widely prescribable to various age groups, thereby being usable as a pharmaceutical composition for promoting the growth of longitudinal bone length and thickness. An indirubin derivative according to the present invention has prevention or treatment effects through oral administration. In addition, unlike conventional therapeutic agents, the pharmaceutical composition for preventing or treating bone diseases of the present invention is a stable compound, which is known to be substantially noncytotoxic to the human body, and is a material of which adverse effects have not been identified and has excellent treatment effects for bone diseases and osteogenesis imperfecta.

8 Claims, 5 Drawing Sheets

(56) References Cited

OTHER PUBLICATIONS

Ichimaru Yoshimi et al: 5-Bromoindirubin 3'-(0-oxiran-2-ylmethyl)oxime: A long-acting anticancer agent and a suicide inhibitor for epoxide hydrolase Bioorganic & Medicinal Chemistry, Elsevier, NL, Jul. 8, 2017.
English translation of the Notice of Reasons for Rejection for Japanese Application No. 2020-507967, dated Nov. 9, 2020, 5 pages.
Chemistry & Biology, Indirubin Derivatives Modulate TGFB/BMP Signaling at Different Leverts and Trigger Ubiquitin-Mediated Depletion of Nonactivated R-Smads, Cheng et al., 2012, 14 pages.
International Preliminary Reporton Patentability received for PCT Patent Application No. PCT/KR2018/004201, dated Oct. 31, 2019, 10 pages ( 7 pages of English Translation and 3 pages of Original Document).
International Search Report and Written Opinion received for PCT Patent Application No. PCT/KR2018/004201, dated Jul. 31, 2018, 12 pages (6 pages of English Translation and 6 pages of Original Document).

* cited by examiner

PHARMACEUTICAL COMPOSITION CONTAINING INDIRUBIN DERIVATIVE AS ACTIVE INGREDIENT

CROSS-REFERENCE TO RELATED APPLICATIONS

This application is a U.S. National Phase filing of PCT/KR2018/004201, filed Apr. 10, 2018, which claims the benefit of Korean Application No. KR 10-2017-0049658, filed Apr. 18, 2017.

TECHNICAL FIELD

The present invention relates to a composition for promoting bone length growth and/or bone thickness increase comprising an indirubin derivatives as active ingredients, for preventing or treating the bone length growth disorders and/or bone density-related diseases comprising an indirubin derivative as an active ingredient.

BACKGROUND ART

Bones are the hardest tissues that make up the human skeleton and have a large amount of bone matrix, which is present throughout the body and plays pivotal roles. From infancy to adulthood, the longitudinal bones that make up the arms and legs to grow in length and determine the height of our bodies. This process is caused by chondrocytes in the bone growth plate, and it is important to grow in adolescent period because the growth plate is limitedly open. Throughout the puberty, the growth plate gradually closes, and as adulthood, bone growth does not occur anymore, but bones still support the body by maintaining the thickness of the bone, or bone density, through continuous metabolic processes. In this process, bone is formed and decomposed by osteoblast and osteoclast, respectively, and the balance between these two cells is important for maintaining bone density and preventing fracture.

In this way, bones are involved in the overall development of our body, structurally maintain the shape of the body, protect the internal organs, physiologically maintain their blood levels and supply new blood as a reservoir of minerals such as calcium and phosphorus. Therefore, abnormal bone development or metabolic abnormalities can lead to various diseases such as precocious puberty, dwarfism, osteoporosis, rickets, osteomalacia, osteomyelia, epithelial hyperplasia and Bezett's disease. It is necessary to understand that the bone formation process is divided into 1) length increase caused by chondrocytes, and 2) bone density increase by balancing osteoblasts and osteoclasts. These two processes are different, and the increase in length determines the height of a person while the increase in bone density is associated with many metabolic bone diseases.

Currently, most of these treatments for bone disease are limited to hormone medicines. Height growth accelerator related to bone length is the only growth hormone used clinically, and the treatment of osteoporosis associated with bone density is the only parathyroid hormone used. However, growth hormone injections are not suitable for children with normal hormonal secretions, but rather have adverse effects such as thyroid dysfunction and hyperplasia and are expensive and not easy to use. In addition, the clinically available therapeutic agent for osteoporosis is the only FDA-approved recombinant parathyroid hormone drug and its analogues, which is also limited to patients with severe osteoporosis of the spine. Furthermore, parathyroid hormone has a limit to the maximum treatment period of 2 years due to concerns about the development of hypercalcemia, as it has a great effect on the metabolism of calcium in the body.

Therefore, new therapies need to be developed to overcome the shortcomings of existing bone diseases treatments, and accordingly, drugs based on small molecule compounds also need to be developed. Because conventional hormonal agents or synthetic peptide agents cannot be orally taken, they are cumbersome to be administered by injection and expensive compared to small molecule compounds. Small molecule compounds which can be applied for bone-related diseases and aberrancies can be promising new drugs in the therapeutic market in that they can be administered orally and have cost competitiveness.

DISCLOSURE OF INVENTION

Technical Problem

The present invention has been made in order to solve the above problems. A purpose of the present invention is to provide the composition showing an excellent bone length growth promoting effect and containing an indirubin derivative as an active ingredient, while having little toxicity in vivo.

In addition, the other object of the present invention is to provide a pharmaceutical composition for preventing or treating bone diseases showing excellent bone disease prevention or treatment effect and including indirubin derivatives as an active ingredient with little toxicity in vivo.

Solution to Problem

In order to achieve the above object, the present invention provides a composition for promoting bone length growth and/or bone thickness increase comprising an indirubin derivative as an active ingredient represented by the following formula (1) or (2).

Formula 1

[Formula 2]

The composition is characterized by promoting the proliferation of chondrocytes, differentiation of osteoblasts by activating Wnt/β-catenin signaling via stabilization and nuclear localization of β-catenin in osteoblasts.

The bone length is the length of the longitudinal bone, and the bone thickness is the bone density.

To achieve the above another object, the present invention provides a pharmaceutical composition for preventing or treating bone length growth disorders and/or bone diseases comprising the indirubin derivatives as active ingredients represented by the following formula (1) or (2).

Formula 1

[Formula 2]

The bone length growth disorder is any one or more selected from the group consisting of dwarfism and precocious puberty, the bone disease is any one or more selected from a group consisting of osteoporosis, rickets, osteomalacia, osteomyelia, epithelial hyperplasia and Bezzet's disease. The present invention provides a pharmaceutical composition for preventing or improving bone length growth disorders and/or bone diseases comprising indirubin derivatives as an active ingredient represented by the following formula (1) or (2) to achieve the above another object.

Formula 1

[Formula 2]

Advantageous Effects of Invention

The composition for promoting bone length growth in accordance with the present invention has the promoting effects on both proliferation of chondrocytes and differentiation of osteoblasts, thereby increasing both bone length and thickness (bone density). Therefore, because it has the advantages of a wide range of prescriptions for various age groups, it can be usefully used as a pharmaceutical composition that can promote the growth of bone length and thickness.

The indirubin derivative according to the present invention has excellent preventive or therapeutic effects by oral administration and is competitive in price unlike conventional hormone-based therapeutic agents.

In addition, the pharmaceutical composition for preventing or treating bone diseases of the present invention is a stable compound which has been found to have little toxicity to the human body, unlike conventional therapeutic agents, and has no confirmed adverse effects and has excellent therapeutic efficacy.

BEST MODE FOR CARRYING OUT THE INVENTION

Hereinafter, various aspects and examples of the present invention will be described in more detail.

One aspect of the present invention relates to a pharmaceutical composition for promoting bone growth comprising indirubin derivatives as an active ingredient represented by Formula 1 or Formula 2.

Formula 1

[Formula 2]

Indirubin is an indigoide compound that exhibits a red color with very similar chemical structure to indigo. In general, a small amount of indirubin is produced as by-product in the process of producing indigo, a blue dye using polygonum tinctorium and isatis tinctoria. Danggui Longhui Wan, a traditional Chinese medicine prescription, consists of 11 kinds of medicines that have been used to treat chronic leukemia. Among them, indirubin has been found to be an effective drug, and recently, it has been known to be a drug of great potential as a cell cycle inhibitor for treating chronic leukemia and neurodegenerative diseases such as Alzheimer's (Bri J. Haemato, 130: 681-690, 2005 Nature Cell Biol, 1: 60-67, 1999). Indirubin as a precursor can form various derivatives, such as an indirubin oxime derivative, an indirubin hydrazone derivative, an indirubin N-acetyl derivative and an indirubin amine derivative.

In the present invention, 5,6-dichloroin dirubin-3'-methoxime (Formula 1) and 5-methoxyoxydidivin-3'-oxime (Formula 2) as active ingredients among the indirubin derivatives minimize the side effects that can occur by administration of conventional hormone agents, are not toxic to osteoblasts and chondrocytes, have a significant effect of increasing the length of the long bone by about two times (180%) relative to the control group, and increase the bone density, that is, the bone thickness by promoting the proliferation of cells and differentiation of osteoblasts.

In addition, according to the present invention, the indirubin derivative represented by Formula 1 or Formula 2 increases the length of the longitudinal bone more than 37¾ times compared to SB415286 (Sigma aldrich) in the ex-vivo culture system.

Therefore, the 5-methoxylindirubin-3'-oxime represented by the formula (1) according to the present invention can be applied to patients of different ages unlike other drugs because they may have efficacy on bone growth, bone thickness, or both, and these effects are more than 30% more significant than those of other indirubin derivatives.

Specifically, the 5,6-dichloroindirubin-3'-methoxime or 5-methoxylindirubin-3'-oxime promotes proliferation of chondrocytes, differentiation of osteoblasts and β-catenin stabilization in osteoblasts as described in the experimental example below.

Specifically, the indirubin derivatives of Formula 1 or Formula 2 in the present invention (5,6-dichloroin dirubin-3'-methoxime or 5-methoxylindirubin-3'-oxime) as new small molecular compounds promote the tibial length in the ex vivo culture system and the activity of ALP, an important marker for bone density increase through the osteoblast differentiation system. In addition, it was confirmed that β-catenin, a key component of the Wnt/β-catenin signaling system which is important for bone formation in chondrocytes and osteoblasts, was stabilized, activated and nuclear-localized after treatment of these drugs.

Therefore, the composition of this study could be utilized as a pharmaceutical composition showing excellent efficacy against bone diseases consisting of osteoporosis, muskosis, rickets, osteomalacia, osteomyelia, epithelial hyperplasia, Bezette's disease, and bone length growth disorder such as short statue, dwarfism, cretinism and precocious puberty.

When an indirubin derivative represented by Formula 1 (5,6-dichloroindirubin-3'-methoxime) and an indirubin derivative represented by Formula 2 (5-methoxylindirubin-3'-oxime) were orally administered to a mouse for toxicity studies, they are considered to be safe substances because the 50% lethal dose (LD 50) of them are at least 1,000 mg/kg.

The bone length means the length of the longitudinal bone, and the bone thickness means the bone density.

Indirubin derivatives of the general formula (1) or formula (2) in the present invention are compositions that can be used for long time because there is little toxicity and adverse effects.

The composition of the present invention preferably comprises 0.1 to 50 parts by weight of the indirubin derivatives represented by Formula 1 or Formula 2 with respect to the total weight of the composition but is not limited to these.

Another aspect of the present invention relates to pharmaceutical compositions comprising indirubin derivatives represented by Formula 1 or Formula 2 as active ingredients for preventing or treating bone length growth disorder and bone disease.

In the description of the indirubin derivatives of the formula (1) or (2), the description overlapping with the above description will be omitted.

"Prevention or treatment of bone disease," a term used in the present invention includes the prevention and complete or partial treatment of bone disease achieved by administering the compositions according to the present invention. It also includes any changes in the patients that reduce or improve symptoms of bone disease, relieve pain, reduce the incidence of bone disease and increase the outcome of treatment.

The bone length growth disorder may be any one or more selected from the group consisting of dwarfism and precocious puberty.

The bone disease may be any one or more selected from the group consisting of osteoporosis, rickets, osteomalacia, osteomyelia, epithelial hyperplasia and Bezzet's disease.

The pharmaceutical compositions of the present invention are pharmaceutical compositions for preventing or treating bone length growth disorders and/or bone diseases. 5,6-dichloroindirubin-3'-methoxime represented by Formula 1 and 5-methoxylindirubin-3'-oxime represented by Formula 2 promote proliferation of chondrocytes and differentiation of osteoblasts and have an excellent prophylactic or therapeutic effect against bone length growth disorders or bone diseases or both by activating stabilization and nuclear localization of β-catenin in osteoblasts.

In other words, they can be applied to patients of various ages because they may have effects on bone length growth or bone thickness increase, or both, and these effects were confirmed to have an excellent effect over the significant numerical range than other indirubin derivatives.

The pharmaceutical compositions of the present invention may further include suitable carriers, excipients and diluents commonly used in the preparation of pharmaceutical compositions. Pharmaceutical dosage forms of the indirubin derivatives of Formula 1 or Formula 2 of the present invention may also be used in the form of their pharmaceutically acceptable salts.

Indirubin derivatives of the formula (1) or formula (2) of the present invention are compositions that can be used for long time because there is little toxicity and adverse effects. The pharmaceutical composition of the present invention preferably comprises 0.1 to 50 parts by weight of the indirubin derivative represented by Formula 1 or Formula 2 with respect to the total weight of the composition, but is not limited to these.

The pharmaceutical compositions of the present invention may be used in the form of oral dosage forms, external preparations, suppositories, and sterile injectable solutions, such as powders, granules, tablets, capsules, suspensions, emulsions, syrups, and aerosols, respectively, according to conventional methods. Carriers, excipients and diluents that may be included in a composition comprising an indirubin derivative of Formula 1 may include lactose, textrose, sucrose, sorbbi, manny, xyl, erythri, malty, starch, Acacia rubber, alginate, gelatin, calcium phosphate, calcium silicate, cellulose, methyl cellulose, microcrystalline cellulose, polyvinyl pyrrolidone, water, methylhydroxy benzoate, propyl hydroxy benzoate, Talc, magnesium stearate and mineral oil. When formulated, diluents or excipients such as commonly used layering agents, extenders, binders, wetting agents, disintegrating agents and surfactants are used. Solid preparations for oral administration include tablets, pills, powders, granules, capsules, and the like, and such solid preparations include at least one excipient such as starch, calcium carbonate, or the indirubin derivative of Formula 1 or Formula 2 above. It is prepared by mixing (calcium carbonate), sucrose or lactose, gelatin and the like. In addition to simple excipients, lubricants such as magnesium stearate and talc are also used. Liquid preparations for oral use include suspensions, solutions, emulsions, and syrups, and may include various excipients, for example, wetting agents, sweeteners, fragrances, and preservatives, in addition to phyquiquid paraffin, which is a commonly used simple diluent. Formulations for parenteral administration include sterile aqueous solutions, non-aqueous solvents, suspensions, emulsions, lyophilized preparations, suppositories. As the non-aqueous solvent and suspending agent, propylene glycol, polyethylene glycol, vegetable oils such as olive oil, injectable esters such as ethyl oleate and the like can be used. As the base of the suppository, witepsol, macrogol, tween 61, cacao butter, laurin butter, glycerogelatin and the like can be used.

Preferred dosages of the pharmaceutical compositions of the present invention vary depending on the condition and weight of the patient, the extent of the disease, the form of the drug, the route of administration and the duration, and may be appropriately selected by those skilled in the relevant field of technology. However, for the desired effect, the composition of the present invention is administered at 0.0001 to 2000 mg/kg, preferably 0.001 to 1000 mg/kg per day. The concentration of the indirubin derivative of Formula 1 or Formula 2 is in the range of 1 nM to 1M, or 1 µM to 1 mM, or 0.1 mM to 0.2 mM, or 0.05 µM to 5 µM, but is not limited to this. Medication may be administered once a day or several times. The dosage above does not limit the scope of the invention in any aspect.

The pharmaceutical composition of the present invention can be administered to mammals such as rats, mice, livestock, humans by various routes. All modes of administration can be expected, for example, by oral, rectal or intravenous, intramuscular, subcutaneous, intrauterine dural or intra-cerebroventricular injection.

Another aspect of the present invention relates to preservatives or improved food compositions for preventing or improving bone length growth disorders and/or bone diseases comprising an indirubin derivative represented by Formula 1 or Formula 2 as an active ingredient.

The term "improvement" used in the present invention means any actions that reduce the level of the parameter associated with the condition to be treated, such as the extent of symptoms.

The food composition of the present invention can be used in various ways, such as drugs, food and beverages for treating bone length growth disorder or bone disease or both. Foods to which the compound of the present invention may be added include, for example, various foods, beverages, gums, teas, vitamin complexes, health supplements, and the like, and may be used in the form of powders, granules, tablets, capsules, or beverages.

The amount of the compound in the food or beverage of the present invention is generally added to the food composition to 0.01 to 15% by weight of the total food, and the health beverage composition is 0.02 to 5 g, preferably 0.3 to 1 g based on 100 ml.

The food compositions of invention, if manufactured as a beverage, is essential at the rate indicated, and there is no specific restriction on the liquid composition, such as ordinary drinks, and may contain several flavoring agents or natural carbohydrates as an additional ingredient. Examples of natural carbohydrates described above are monosaccharides (e.g. glucose, fructose and the like), disaccharides (e.g. maltose, sucrose and the like), and polysaccharides (e.g. dextrin and cyclodextrin, as well as common sugars such as xylitol, sorbitol and erythritol). As flavoring agents other than those described above, natural flavoring agents (e.g. taumatine, stevia extracts, such as fume-based A and glycirrhizine, and synthetic flavoring agents, such as sakarin, aspartame) can be advantageously used. The ratio of the above natural carbohydrates is generally about 1 to 20 g per 100 ml of the composition of this invention and, preferably, about 5 to 12 g.

In addition to the above, the composition of the present invention includes various nutrients, vitamins, minerals (electrolytic qualities), flavors such as synthetic flavors and natural flavors, coloring and neutralizing agents (such as cheese, chocolate), pectic acid and its salts, alginic acid and its salts, organic acids, protective colloidal thickeners, pH adjusting agents, stabilizers, preservatives, glycerin, alcohols, carbonation agents used in carbonated beverages, and the like.

The compositions of the present invention may also contain pulp to produce natural fruit juices, fruit juice beverages and vegetable beverages. These components can be used independently or in combination. The proportion of such additives is not so critical but is generally selected in the range of 0 to about 20 parts by weight per 100 parts by weight of the composition of the present invention.

MODE FOR THE INVENTION

This invention is to be explained in more detail by example, below, but the scope and contents of this invention cannot be interpreted as it is reduced or limited. In addition, it is clear that this invention can be easily carried out by the usual technician, whose results have not been specifically presented, provided that it is based on the initiation of this invention, including any of the following practices, and that these modifications and modifications are within the scope of the patent claims.

In addition, the experimental results presented below are only representative of the experimental results of the above Examples and Comparative Examples, and the each effect of the various embodiments of the present invention not explicitly set forth below will be described in detail in the corresponding sections.

EXAMPLE 1. SYNTHESIS OF 5,6-dichloroindirubin-3'-methoxime (A3051)

① Synthesis of Intermediate 5',6'-Dichloro-[2,3'-Biindolysilidine]-2'3-Dion (5',6'-dichloro-[2,3'-biodolydene]-2',3-dione]

indoxyl acetate

5,6-dichloroisatin

5',6'-dichloro-[2,3'-biindolinylidene]-2',3-dione

Dissolve in MeOH (92.80 ml) and add phosphoxyl acetate (405.48 mg, 2.315 mmol) and sodium carbonate (Na2CO3) (637.83 mg, 6.02 mmol) for 12 hours at 65° C. Check the termination of the reaction using TLC (Rf=0.4; ethylacetate/hexane=½ (v/v)) and cool the product until a crystalline mass is formed in the ice. When crystals form, filter them out, remove the solvent, discard the filtrate and rinse the product several times with a solvent (Ethanol/Water=1/1(v/v)). The product was filtered to dry in the vacuum pump and used in the next step without further purification.

② Synthesis of A3051

A3051

Put 5'6'-dichloro-[2,3'-biodinylidine]-2'3-dion (5',6'-dichloro-[2,3'-biedolinylidene]-2',3-dione (600 mg, 1.81 mmol) in a 100 ml round bottom flask and then put the pyridine (151 ml). Add H2NOCH3.HCl (3026.4 mg, 36.24 mmol) and stir for 12 hours at 120° C. Use TLC (Rf=0.4 and ethylacetate/hexane=1/1(v/v)) to verify the termination of the reaction and reduce the temperature of the reaction solution to room temperature. After evaporating all the pyridine solvents of the product, add water and ethyl acetate to dissolve the product using ultrasonic waves for 30 minutes. Extract it twice with ethyl acetate et al. Wash it with a saturated solution of NaHCO3. After taking the extracted solution with anhydrous magnesium sulfate, evaporate the solvent and reset it using methanol and nucleic acid. If the product is dried in the vacuum pump, a red solid A3051 can be obtained with a yield of 47.94% (326 mg). $^1$H NMR (400

MHz, DMSO-d6) δ 11.36 (s, 2H), 8.80 (s, 1H), 8.08 (d, 1H, J=7.7 Hz), 7.46-7.41 (m, 2H), 7.07-6.99 (m, 2H), 4.38 (s, 3H).

EXAMPLE 2. SYNTHESIS OF 5-methoxylindirubin-3'-oxime (A3334)

① Synthesis of Intermediate 5'-Metoxi-[2,3'-Bindolynylidine]-2',3-dion (5'-methoxy-[2,3'-biodolylene]-2',3-dione)

indoxyl acetate

5-methoxyisatin

5'-methoxy-[2,3'-biindolinylidene]-2'-3-dione

Add 5-methoxyisatin (1000 mg, 5.65 mmol) in a 250 ml round bottom flask and dissolve it in MeOH (225 ml). Add indoxyl acetate (989 mg, 5.65 mmol) and sodium carbonate (Na2CO3) (1496 mg, 14.11 mmol) to stir at 65° C. for 12 hours. Check the termination of the reaction using TLC (Rf=0.4; ethylacetate/hexane=½ (v/v)) and cool the product until a crystalline mass is formed in the ice. After crystals form, filter them out, remove the solvent, discard the filtrate and rinse the product several times with a solvent (Ethanol/Water=1/1(v/v)). Generated water was filtered to dry in a vacuum pump and then used in the next step without further purification.

② Synthesis of A3334

5'-methoxy-[2,3'-biindolinylidene]-2'-3-dione

A3334

Put 5'-methoxy-[2,3'-bindolinylidine]-2",3-dion (5'-methoxy-[2,3'-bindolylidene]-2',3-dione (670 mg, 2.29 mmol) in a 100 ml round bottom flask and dissolve it in pyridine (phyridine) (27 ml). Add H2NOH.HCl (3186 mg, 45.85 mmol) and stir for 12 hours at 120° C. Use TLC (Rf=0.5 and ethylacetate/hexane=1/1(v/v)) to verify the termination of the reaction and reduce the temperature of the reaction solution to room temperature. After evaporating all the pyridine solvents of the product, add water and ethyl acetate to dissolve the product using ultrasonic waves for 30 minutes. Extract it twice with ethyl acetate et al. Wash it with a saturated solution of NaHCO3. After dehydrating the extracted solution with anhydrous magnesium sulfate, evaporate the solvent and reset it using methanol and nucleic acid. If the product is dried in the vacuum pump, a red solid A3334 can be obtained at a yield of 59% (420 mg). $^1$H NMR (400 MHz, DMSO-d6) δ 13.52 (s, 1H), 11.79 (s, 1H), 10.54 (s, 1H), 8.35 (d, J=1.5 Hz, 1H), 8.26 (d, J=7.6 Hz, 1H), 7.41 (d, J=2.8 Hz, 2H), 7.08-7.00 (m, 1H), 6.82-6.71 (m, 2H), 3.78 (s, 3H).

COMPARATIVE EXAMPLES 1-12. SYNTHESIS OF THE INDIRUBIN DERIVATIVES 5-chloroindirubin-3'-methoxime, 5-bromoindirubin-3'-oxime, 5-bromoindirubin-3'-methoxime, 5-bromoindirubin-3'-ethoxyme, 6-Bromo indiru-3'-oxime, 6-chloro-5-nitroindirubin, 6-chloro-5-nitroindirubin-3'-oxime, 6-chloroindirubin-3'-methoxime, 5,6-dichloroindirubin, 5,6-dichloroindirubin-3'-oxime, 5,6-dichloroindirubin-3'-propyl oxime were synthesized in the same manner as 5,6-dichloroindirubin-3'-methoxime or 5-methoxyoxyindirubin-3'-oxime, which was dissolved in dimethyl sulfide (DMSO) and applied to the experiment. It was named Comparative Examples 1-12 in order.

| No. | Structure formulas | Compound |
|---|---|---|
| Example 1 |  | indirubin-3'-oxime |
| Example 2 |  | 5-chloroindirubin-3'-methoxime |
| Example 3 |  | 5-bromoindirubin-3'-oxime |
| Example 4 |  | 5-bromoindirubin-3'-methoxime |
| Example 5 |  | 5-bromoindirubin-3'-ethyloxime |
| Example 6 |  | 6-bromoindirubin-3'-oxime |

-continued

| No. | Structure formulas | Compound |
|---|---|---|
| Example 8 | | 6-chloro-5-nitroindirubin-3'-oxime |
| Example 9 | | 6-chloroindirubin-3'-methoxime |
| Example 10 | | 5,6-dichloroindirubin |
| Example 11 | | 5,6-dichloroindirubin-3'-oxime |
| Example 12 | | 5,6-dichloroindirubin-3'-propyloxime |

Experimental Apparatus and Methods

1. Cell Culture

1) ATDC5 Cell Culture

The ATDC5 cell (Murine constant cell line) was cultured in the DMEM (Dulbecco's modified Eagle's medium, Gibco, Grand Island, N.Y.) containing 5% Fetal Bovine Serum (FBS) and 1% penicillin/streptomycin under conditions of 37° C. and 5% $CO_2$.

2) MC3T3-E1 Cell Culture

The MC3T3-E1 cell (Mouse osteoblastic cell line) was cultivated under conditions of 37° C. and 5% $CO_2$ at the minimal essential media (α-MEM) (Gibco) containing 10% prenatal serum and 1% penicillin/streptomycin. For the test of differentiation induction, cells were cultivated in α-MEM mediums containing 50 μg/ml ascorbic acid and 100 mM β-glycerophosphate.

2. MTT Reduction Analysis

When the cells were stably attached after $5 \times 10^3$ ATDC5 cells were stuck in 96 well plate, the drug (here is 6-bromoindirubin-3'-oxime) was treated. After 24 hours, transfer to a medium containing 100 μg/ml MTT [3-(4,5-dimethyl-thiazol-2-yl)-2,5-diphenyletrazoliumbromide)] and incubate the cells for 2 hours before removing the growth medium. The MTT, which was reduced to purple formazan, was dissolved with DMSO and then excreted at 540 nm by ab absorbance measurement.

3. Western Blot Analysis

For Western blot analysis, drugs (here are 5,6-dichloroindirubin-3'-methoxime, 5-methoxylindirubin-3'-oxime) were treated 24 hours, and MC3T3-E1 cells were cultured and harvested in a culture dish to reach 100% confluency. Harvested samples for immunoblot was performed to quantify the protein was after cell lysis, using SDA-PAGE gel using the antibody after electrophoresis.

4. Immunocytochemistry

Drugs (here are 5,6-dichloroindirubin-3'-methoxime, 5-methoxylindirubin-3'-oxime) were treated for 24 hours when the cells were securely attached to the cover glass that was placed in the 12 well plate at a density of $2.5 \times 10^4$ cells per well. Cells were cleaned with phosphoric acid buffer solution and fixed at room temperature for 20 minutes by adding 4% paraformaldehyde, and then a protein expressed in the cells was observed through the process of permeabilization, blocking and immunofluorescence.

5. ALP Activity Assay $5 \times 10^4$ MC3T3-E1 cells were incubated on a 24 well plate for two days and stuck. After confirming that the cells reached 100% confluency, the medications (5,6-dichloroindirubin-3'-methoxime in Example 1) were treated in the differentiation medium for 48 hours. The cells were cleaned with a phosphoric acid buffer solution and the samples harvested were treated with a buffer solution (pH 10.3) containing 50 mM Tris-chloric acid, 100 mM glisin and p-nitro phenylpospate after cell lysis. For analysis, 3 M sodium hydroxide was treated, and absorbance was measured at 405 nm. The ALP activity was quantified by measuring the protein concentration using Bradford Analyzer.

6. Tissue Culture and Reagents

Longitudinal bones were isolated from 15.5 embryonic day C57BL/6 mice and incubated for 7 days in a 24-well tissue culture dish. Medium was used as Minimal Essential Medim (α-MEM, Gibco) including 10% fetal bovine serum (FBS), 1 mM beta polyglycerol disodium phosphate, 50 ng/ml ascorbic acid, 0.3 g/L-glutamine, 0.2% BSA, 100 U/ml penicillin, 100 μg/ml streptomycin. After the longitudinal bone was separated from the mouse, the longitudinal bone isolated from the medium was incubated for 24 hours, and the drug was treated. The medium and the drug (here are Example 1, Example 2, Comparative Examples 1, 7-9 and indirubin derivatives of 10-12) were changed every other day. The length of the longitudinal bone was measured before and after treatment with the drug. The longitudinal bone tissue after drug treatment was marched with PBS and fixed using 4% formaldehyde.

Figure 1:
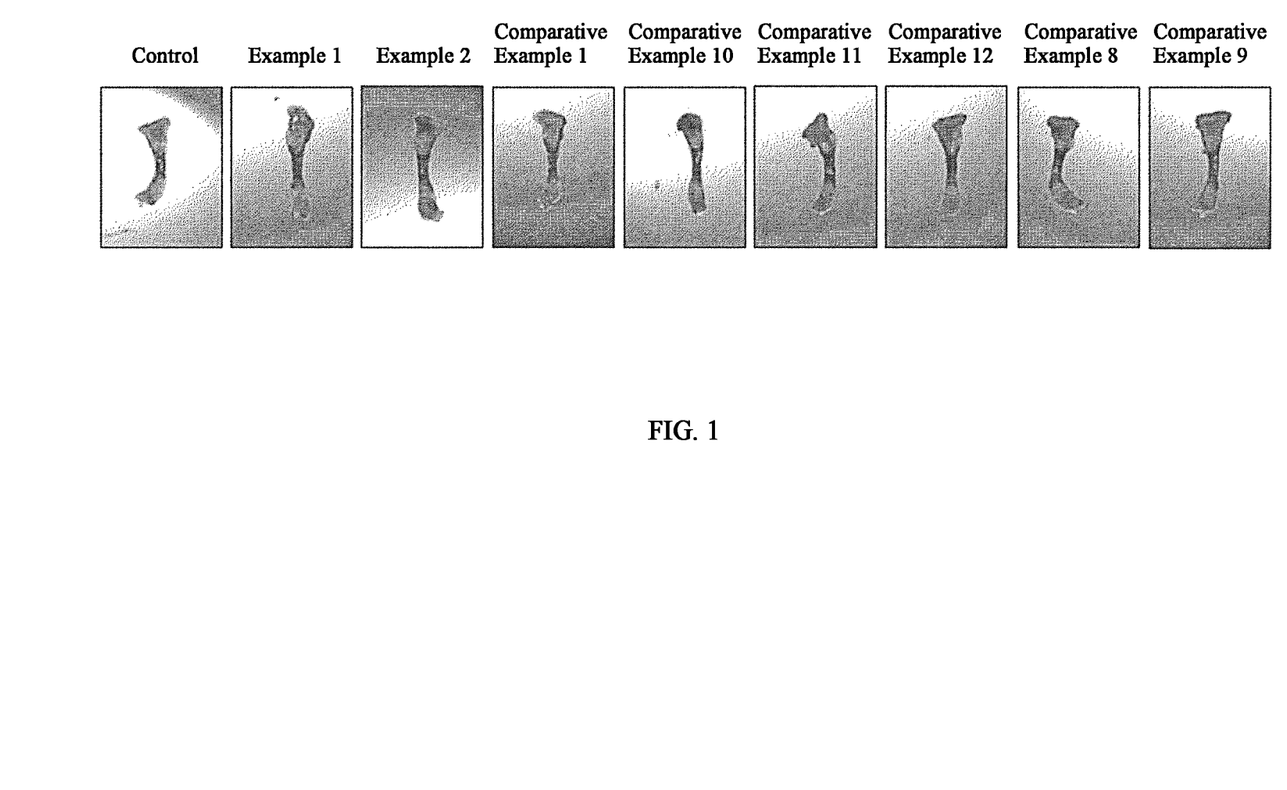
FIG. 1 is a photograph of longitudinal bone growth when cultured ex vivo and treated with indirubin derivatives in Examples 1, 2 and Comparative Examples 1, 8, 9, 10-12.
Figure 2:
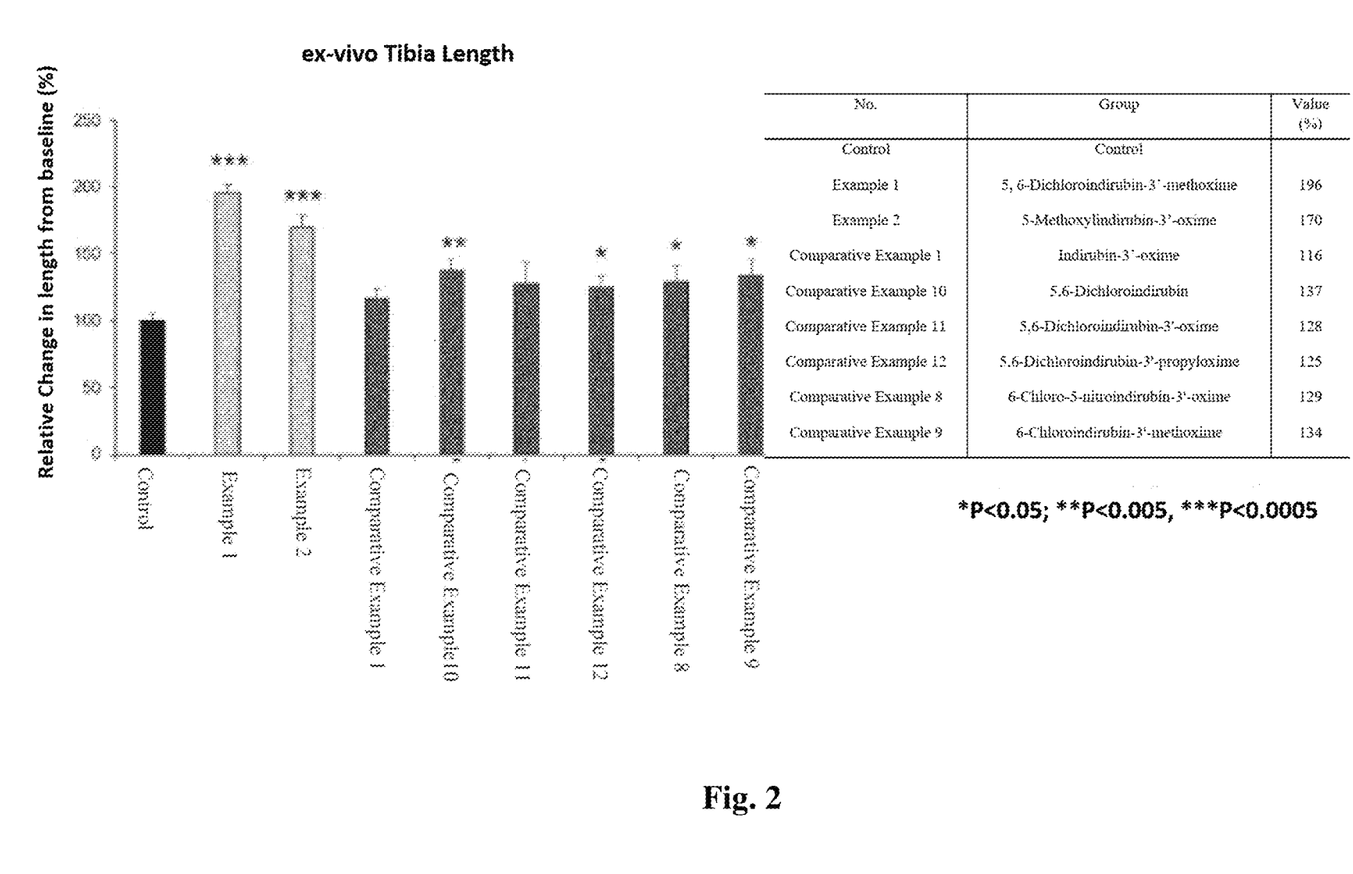
FIG. 2 is a graph and table showing the changes in the length of the longitudinal bone measured in FIG. 1. Indirubin derivatives were treated as 0.5 μM, respectively, in culture medium for 6 days.

In order to more precisely determine the effect of indirubin derivatives in Example 1 or Example 2 of the present invention and other indirubin derivatives on the culture of ex-vivo longintudinal bone, various indirubin derivatives (Examples 1 and 2 and comparison Example 1, 8, 9, 10-12 indirubin derivatives) were treated as in Experimental Method 6, and the length of the longitudinal bone was measured.

FIG. 1 is a photograph of the longitudinal bone cultured at each ex-vivo when treated with indirubin induction in Example 1, Example 2, and Comparison Example 1, 8, 9, 10-12. FIG. 2 is a graph and table showing the variation in the length of the longitudinal bone measured in FIG. 1. In this case, the drooping indirubin derivatives were identical at 0.5 μM and treated in culture medium for 6 days.

This can be confirmed that these effects by 5,6-dichloroindirubin-3'-methoxime in Example 1 and 5-methoxylindirubin-3'-oxime in Example 2 are significantly superior to those by the indirubin derivatives of Comparative Examples 8, 9 and Comparative Examples 10-12. Specifically, the length of the longitudinal bone was found to be increased by about 54% more effectively by these two molecules in accordance with this invention. This difference in the length of the long bones is a very significant improvement, which is much faster than conventional hormonal agents that are expected to be able to grow longitudinal bones. The control group (control) is a measure of the length of long bones treated with DMSO solution instead of the drug.

Figure 3:
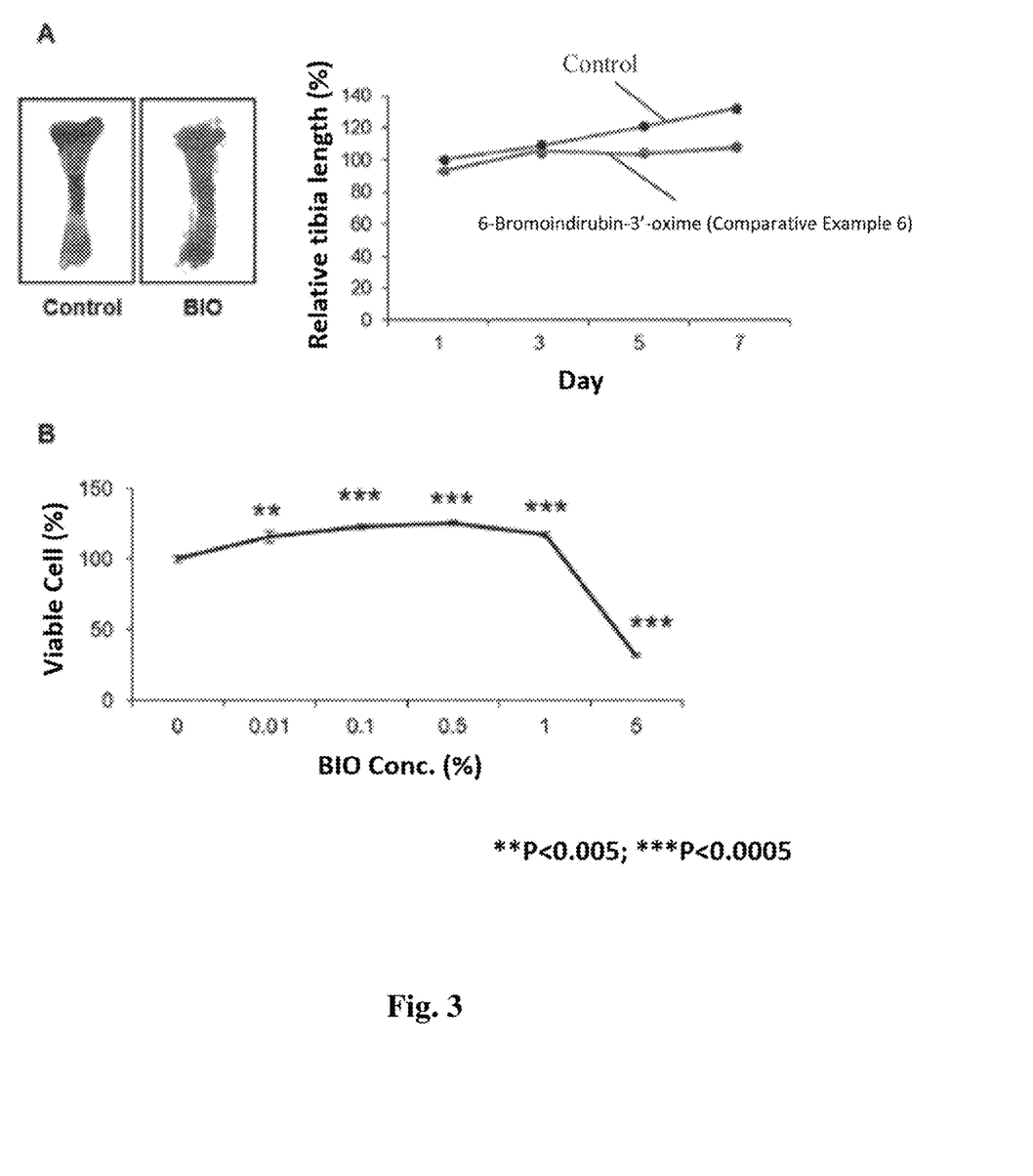
FIG. 3A is a photograph (left) of a longitudinal bone growth when cultured ex vivo and treated with 6-bromoindirubin-3'-oxime in Comparative Example 6 and a graph (right) that quantitatively shows this growth.
FIG. 3B is a graph of MTT analysis of chondrocytes according to different bromoin dirubin-3'-oxime concentration to verify if the reduction in the length of longitudinal bone treated with 6-bromoindirubin-3'-oxime in Comparative Example 6 are related to the effect on the viability of chondrocytes.

We sought to determine more accurately the effect of 6-bromoindirubin-3'-oxime (Comparative Example 6) on the culture of ex-vivo longitudinal bone. FIG. 3A is a photograph (left) of a longitudinal bone culture in ex-vivo and a graph showing the numerical value when treated with 6-bromoindirubin-3'-oxime of Comparative Example 6 (right). At that time, 0.5 μM 6-bromoindirubin-3'-oxime was treated in culture medium for 6 days. The control is longitudinal bone treated with DMSO solution instead of drug.

As shown in FIG. 3A, the length of the ex-vivo longitudinal bone was reduced by treatment of 6-bromoindirubin-3'-oxime in Comparative Example 6 compared to control group.

FIG. 3B is a graph of MTT reduction analysis of chondrocytes after treatment of different concentration of 6-bromoindirubin-3'-oxime to confirm if the reduction in the length of longitudinal bone treated with 6-bromoindirubin-3'-oxime in Comparative Example 6 is related to the effect on the survival rate of chondrocytes.

MTT reduction assay is a method to measure the viability of cells by analyzing the difference in absorbance due to the reduction of yellow MTT to purple formazan caused by mitochondrial enzyme reaction in living cells.

As shown in FIG. 3B, 6-bromoindirubin-3'-oxime (Comparative Example 6) inhibits the growth of chondrocytes when treated at a concentration of 1 μM or more, and survival rate of these cells was confirmed to decrease below 50% by 5 μM 6-bromodirubin-3'-oxime. That is, it suggests that 6-bromoindirubin-3'-oxime in Comparative Example 6 has toxicity to chondrocytes. In other words, 6-bromoindirubin-3'-oxime suppresses the length of longitudinal bones and is toxic to cells, so it could be a problem that this drug will be used as a treatment for bone disease or bone growth disorder.

Figure 4:
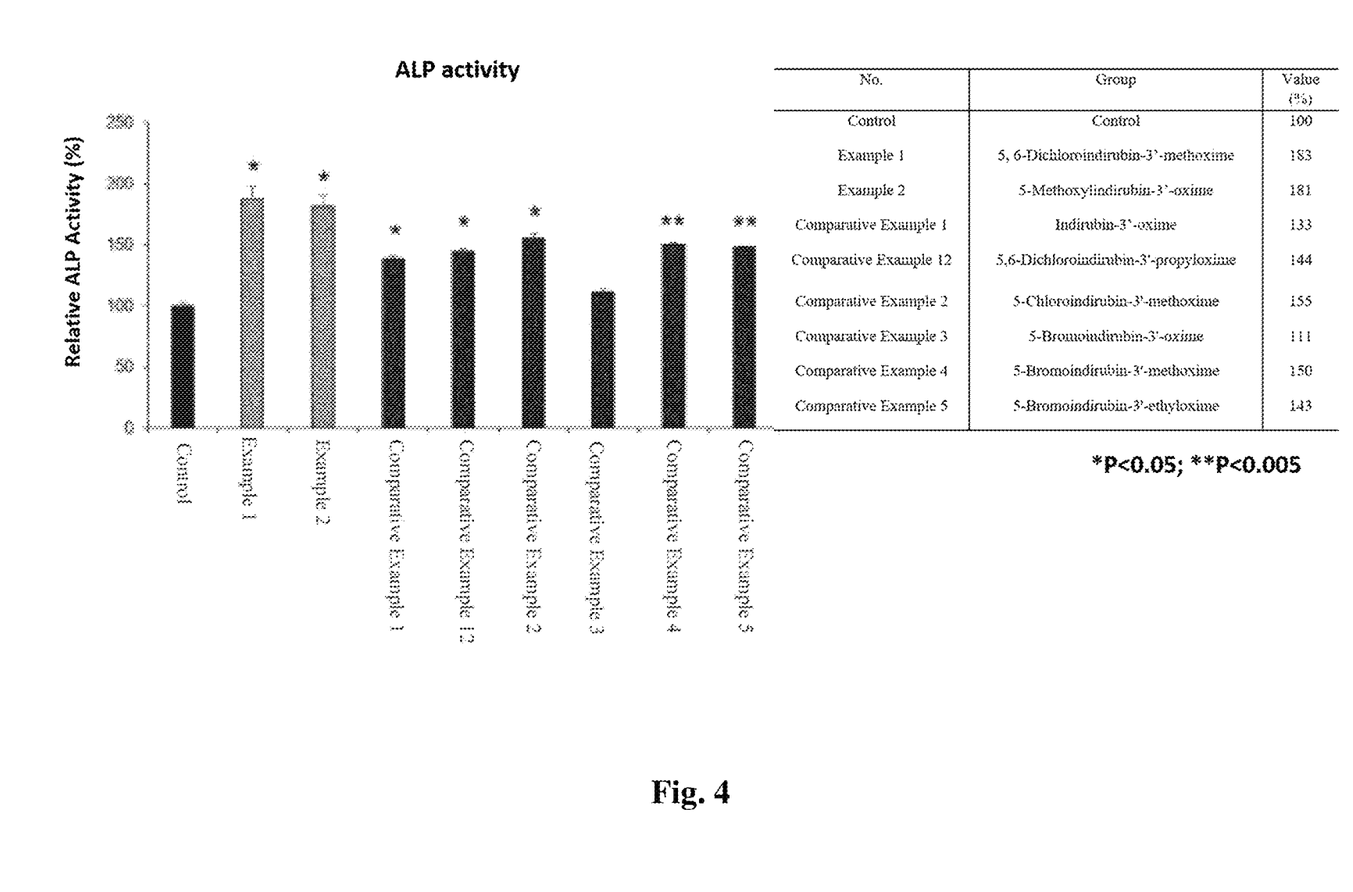
FIG. 4 is a graph and table showing ALP activity in cells treated with 5,6-dichloroin dirubin-3'-methoxime in Example 1, 5-methoxylindirubin-3'-oxime of Example 2, indirubin derivatives in Comparative Examples 1-5 and 12.

ALP activity analysis was performed as Experimental Method 5 to determine the effect of 5,6-dichloroindirubin-3'-methoxime in Example 1 and 5-methoxylindirubin-3'-oxime in Example 2 on bone mineral density. FIG. 4 is a table showing the measured a graph showing ALP activity in cells and a table showing the degree of ALP activity in cells treated with 5,6-dichloroindirubin-3'-methoxime of Example 1 according to the present invention, 5-methoxylindirubin-3'-oxime of Example 2, indirubin derivatives of Comparative Examples 1-5 and 12. The control is the ALP activity in the cells prior to drug treatment.

As shown in FIG. 4, when the activity of ALP (alkaline phosphatase), an important marker for bone formation in differentiation conditions, was analyzed, ALP activity was significantly higher in the group treated with 5,6-dichloroindirubin-3 '-methoxime of Example 1 and 5-methoxyl indirubin-3'-oxime of Example 2 than other groups.

This effect is a very remarkable efficacy that cannot be confirmed by the existing indirubin derivatives (Comparative Examples 1-5, 12), specifically, ALP activity was increased close to 2-fold by the indirubin derivatives of Examples 1 and 2, while the ALP activity was increased by conventional indirubin derivatives only up to 1.5-fold.

In other words, in the case of the 5,6-dichloroindirubin-3'-methoxime of Example 1 or the 5-methoxylindirubin-3'-oxime of Example 2 according to the present invention, the ALP activity, which plays the most important role in bone formation, is improved higher by 30¾ to 100%, thereby confirming that they are the most effective therapeutic agents.

Wnt/β-catenin signaling plays an essential role in the development, growth and homeostasis in vertebrates. In particular, it has been found that an abnormality may occur in the bone formation process in animals including humans if Wnt/β-catenin signaling is dysregulated. β-Catenin is a key signaling molecule in this pathway, which stabilizes and accumulates in the cytoplasm, and then moves into the nucleus to promote expression of various genes related to increase in bone length and density.

Figure 5:
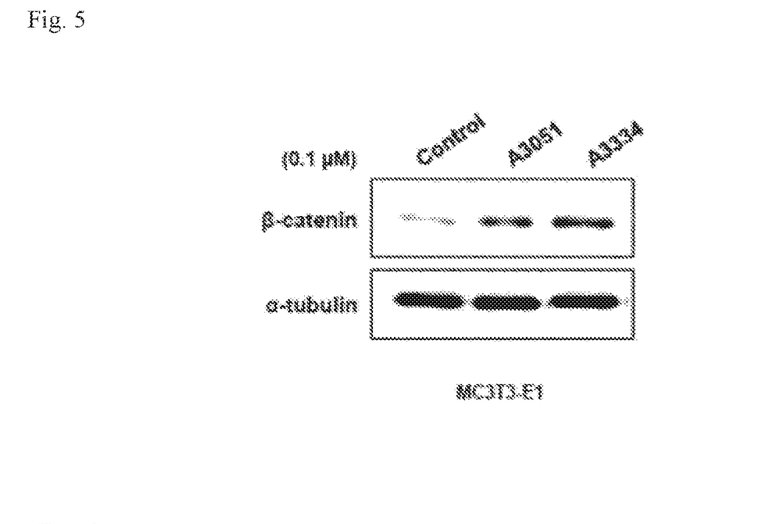
FIG. 5 is a result of western blot analyses for the protein extracts obtained from MC3T3-E1 cells (osteoblast cells) to examine the effect of the 5,6-dichloro indirubin-3'-methoxime (A3051) in Example 1 and the 5-methoxylindirubin-3'-oxime (A3334) in Example 2 on 6-catenin stabilization.

FIG. 5 is the result of Western blot using MC3T3-E1 cells (osteoblast cells) to confirm the effects of 5,6-dichloroindirubin-3'-methoxime of Example 1 and 5-methoxyindirubin-3'-oxime of Example 2 on the stability of β-catenin.

As shown in FIG. 5, the 5,6-dichloroin dirubin-3'-methoxime of Example 1 and the 5-methoxylindirubin-3'-oxime of Example 2 significantly induced the stabilization of β-catenin.

Figure 6:
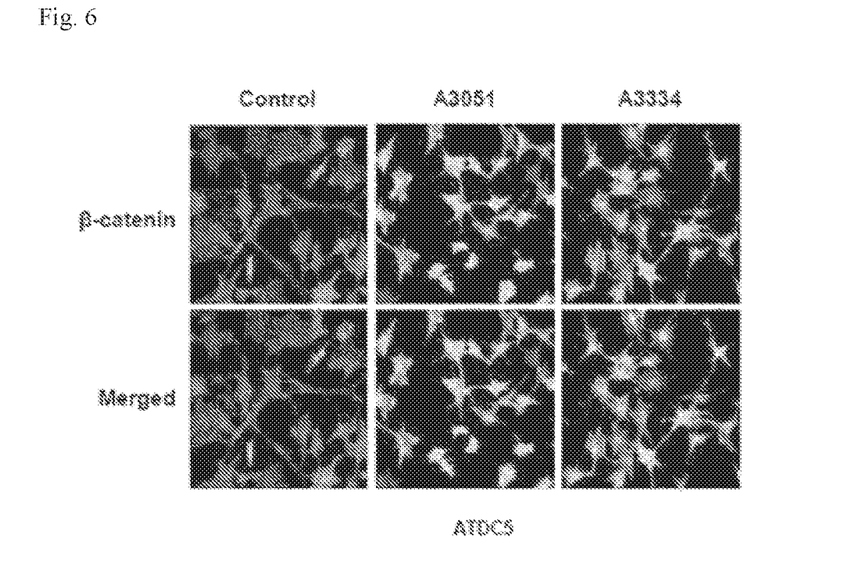
FIG. 6 is a photograph confirming the expression and localization of β-catenin in ATDC5 cells treated with 5,6-dichloroindirubin-3'-methoxime (A3051) in Example 1 and the 5-methoxylindirubin-3'-oxime (A3334) in Example 2 through Immunocytochemistry.

We confirmed if the β-catenin stabilization by 5,6-dichloroin dirubin-3'-methoxime of Example 1 and the 5-methoxylindirubin-3'-oxime of Example 2 significantly eventually leads to an increase in the amount of β-catenin which move into the nucleus.

FIG. 6 is a photograph confirming the the β-catenin concentration in the ATDC5 cells treated with 5,6-dichloroindirubin-3'-methoxime of Example 1 and 5-methoxylindirubin-3'-oxime of Example 2 by immunocytochemistry. In other words, the expression and localization of β-catenin in ATDC5 cells were confirmed through ICC.

As shown in FIG. 6, 5,6-dichloroindirubin-3'-methoxime of Example 1 and 5-methoxyindirubin-3'-oxime of Example 2 according to the present invention induce β-catenin stabilization and increase the mobility of the stabilized β-catenin into the nucleus. In other words, the treatment of 5,6-dichloroindirubin-3'-methoxime of Example 1 and 5-methoxylindirubin-3'-oxime of Example 2 increase the overall amount of β-catenin and the amount of β-catenin moved to the nucleus.

Through the experimental results, 5,6-dichloroindirubin-3'-methoxime of Example 1 or 5-methoxyindirubin-3'-oxime of Example 2 improve stabilization of the β-catenin even at low concentrations and increase the amount of β-catenin moved into the nucleus, thereby increasing the expression of various bone formation-related genes and improving bone density as well as bone length.

In conclusion, the above results suggest that the 5,6-dichloroindirubin-3'-methoxime of Example 1 and the 5-methoxylindirubin-3'-oxime of Example 2 could be an effective treatment for various bone diseases by increasing the bone length and density.

The invention claimed is:

1. A method of treating a bone disease or a bone growth disorder, comprising:
   administering to a subject a therapeutically effective dose of or a pharmaceutically acceptable salt thereof, wherein the bone disease or a bone growth disorder is at least one disorder selected from the group consisting of: short stature, dwarfism, cretinism, precocious puberty, osteoporosis, osteomalacia, osteomyelia, epithelial hyperplasia, and Bezzet's disease.

2. The method according to claim 1, wherein the subject is an animal or a human.

3. A method of promoting bone length growth and/or increasing bone density, comprising:
   administering to a subject a therapeutically effective dose of or a pharmaceutically acceptable salt thereof.

4. The method according to claim 3, wherein the bone length growth is measured by an increase in longitudinal bone length relative to a control, or wherein the increase in bone thickness is measured by an increase in bone density relative to the control.

5. The method according to claim 3, wherein the subject is a cell, a tissue, an animal, or a human.

6. The method according to claim 5, wherein the cell is at least one type of cells selected from the group consisting of: chondrocytes and osteoblasts.

7. A method of treating a bone disease or a bone growth disorder, comprising:
administering to a subject a therapeutically effective dose of or a pharmaceutically acceptable salt thereof,
wherein the bone disease or a bone growth disorder is at least one disorder selected from the group consisting of: short stature, dwarfism, cretinism, precocious puberty, osteoporosis, osteomalacia, osteomyelia, epithelial hyperplasia, and Bezzet's disease.

8. The method according to claim 7, wherein the subject is an animal or a human.

* * * * *